(12) United States Patent
Kubo et al.

(10) Patent No.: US 6,679,822 B2
(45) Date of Patent: Jan. 20, 2004

(54) POLYALKYLENE OXIDE-MODIFIED PHOSPHOLIPID AND PRODUCTION METHOD THEREOF

(75) Inventors: Kazuhiro Kubo, Kawasaki (JP); Chika Itoh, Kawasaki (JP); Syunsuke Ohhashi, Yokohama (JP); Tohru Yasukohchi, Yokohama (JP)

(73) Assignee: NOF Corporation, Tokyo (JP)

( * ) Notice: Subject to any disclaimer, the term of this patent is extended or adjusted under 35 U.S.C. 154(b) by 142 days.

(21) Appl. No.: 10/086,430

(22) Filed: Mar. 4, 2002

(65) Prior Publication Data

US 2002/0165205 A1 Nov. 7, 2002

(30) Foreign Application Priority Data

Mar. 2, 2001 (JP) ...................................... P.2001-058160

(51) Int. Cl.$^7$ .................................................. C07F 9/02
(52) U.S. Cl. ............................. 554/82; 554/80; 514/114
(58) Field of Search ...................... 554/80, 82; 514/114

(56) References Cited

U.S. PATENT DOCUMENTS 6,261,537 B1    7/2001   Klaveness et al.

FOREIGN PATENT DOCUMENTS

| WO | WO 98 18500 | 5/1998 |
| WO | WO 98 18501 | 5/1998 |

OTHER PUBLICATIONS

Patent Abstract of Japan, vol. 2002, No. 06, Jun. 4, 2002 and JP 2002 037833, Feb. 6, 2002.
S. Zalipsky et al, "Poly(ethylen gylcol)–Grafted Liposomes with Oligopeptide or Oligosaccharide Ligands Appeaned to the Termini of the Polymer Chains", Bioconjugate Chemistry, American Chemical Society, Washington, U.S., vol. 8, No. 2, Mar. 1997, pp. 111–118.
S.Zalipsky et al, "Long Circulating, Cationic Liposomes Containing Amino–PEG–Phosphatidylethanolamine", FEBS Letters, Elsevier Science Publishers, Amsterdam, NL, vol. 353, No. 1, 1994, pp. 71–74.
T.M. Allen et al, "Liposomes Containing Synthetic Lipid Derivatives of Poly(Ethylene Glycol) Show Prolonged Circulation Half–Lives in Vivo" Biochimica et Biophysica ACTA, Amsterdam, NL, vol. 1066, 1991, pp. 29–36.
Patent Abstracts of Japan, vol. 1998, No. 2, Jan. 30, 1998 and JP 09 278672, Oct. 28, 1997.
Woodle et al., "Versatility in lipid compositions showing prolonged circulation with sterically stablized liposomes" *Biochimica et Biophysica Acta*, 1105 (1992) pp. 193–200.
Samuel Zalipsky "Synthesis of an End–Group Functionalized Polyethylene Glycol–Lipid Conjugate for Preparation of Polymer–Grafted Liposomes" *Bioconjugate Chem 1993*, 4,296–299.

*Primary Examiner*—Deborah D. Carr
(74) *Attorney, Agent, or Firm*—Sughrue Mion, PLLC

(57) ABSTRACT

A polyalkylene oxide-modified phospholipid represented by formula (1) defined in the specification, has a monoacyl phospholipid content of not more than 3% by weight and a content of a base having a nitrogen atom of not more than 0.02% by weight.

36 Claims, No Drawings

POLYALKYLENE OXIDE-MODIFIED PHOSPHOLIPID AND PRODUCTION METHOD THEREOF

BACKGROUND OF THE INVENTION

1. Field of the Invention

The present invention relates to a novel and useful polyalkylene oxide-modified phospholipid, the production method thereof, and the uses thereof, and particularly to a polyalkylene oxide-modified phospholipid, which can be used for the modification or the emulsification of a physiologically active substance or for a drug delivery system such as liposome, etc., the production method and the uses thereof.

2. Description of the Related Art

Recently, the investigations of liposome preparations such as an anticancer agent, etc., have been widely carried out and for the purpose of improving the retentivity thereof in blood, the water-soluble high molecular modification of liposome has been actively carried out. As one of the modifications, liposome-modified polyethylene oxide-modified phospholipids have been used. Since they are used for medicines, it is preferred that they contain impurities as less as possible or they contain no impurities.

In the synthesis reaction of a liposome-modified polyethylene oxide-modified phospholipid, a base containing nitrogen, such as triethylamine, etc., is frequently used as the catalyst. In this case, for removing the base excessively existing after the reaction, it is necessary to make the system acidic. However, during the process, the deterioration of the liposome-modified polyethylene oxide-modified phospholipid occurs and it is difficult to obtain a high-pure product.

Also, a base containing nitrogen, such as triethylamine, etc., frequently has an ammonia smell or a specific smell. Thus, it is desirable that such a base is not used for working environment.

Synthetic methods of polyethylene oxide-modified phospholipids are reported by M. C. Woodle (Biochimica et Biophysica Acta, 1105, 193–200(1992)) and S. Zalipsky (Bioconjugate Chem., 4, 296–299(1994)). Practically, they report a method of, after activating the terminal of polyethylene glycol using 1,1'-carbonyl diimidazole or disuccinimidyl carbonate in an organic solvent, the activated terminal of polyethylene glycol is reacted with a phospholipid in the presence of a base such as triethylamine, etc., and thereafter, the product is purified by a reversed-phase silica gel chromatography, etc., to obtained a polyethylene oxide-modified phospholipid.

In the method, immediately after the reaction, for removing the base such as triethylamine excessively existing, the system is similarly made acidic. In the case, monoacyl phospholipid (generally, is called lysophospholipid) is formed. The monoacyl phospholipid has a strong biotoxicity and it gives a problem in the case of using medicines, for example, in the case of being utilized as a drug delivery system.

Also, when after synthesis, a reversed-phase silica gel chromatography or a dialysis is carried out in a purification process, at emerging from the column in the chromatography, the product is deteriorated (the formation of the above-described monoacyl phospholipid, etc.) and during the dialysis, there occurs a problem that the product is hydrolyzed. Accordingly, in such related art methods, it is difficult to obtained high-pure products, which is also a problem from an industrial viewpoint.

As described above, in the related art methods, the products contain a base such as triethylamine, etc., and when it is intended to remove the impurities, lysophospholipid is contained, whereby it is difficult to obtain high-pure products. Also, in the related art methods, from the points that the yields of the products are bad and a large amount of solvent is used, it is difficult to apply these methods to the industrial production of products.

Accordingly, a simple synthetic method of a polyethylene oxide-modified phospholipid having a high purity without containing impurities such as a base having a nitrogen atom, such as triethylamine, etc., or a monoacyl phospholipid has been desired.

Since a phospholipid has excellent effects as an emulsifier and a humectant, many investigations have been made for compounding with not pharmaceuticals alone but cosmetics, and furthermore such a phospholipid has been investigated as liposome or by the addition of another surface active agent. However, especially in the application to emulsions, cosmetics, etc., by increasing the addition amount of the phospholipid, there occurs a problem that the surface active agent is not dissolved well, whereby the addition amount of the other surface active agent than a phospholipid must be increased.

SUMMARY OF THE INVENTION

An object of the invention is to provide a high-pure polyethylene oxide-modified phospholipid having less contents of impurities such as a base having a nitrogen atom, monoacyl phospholipid, etc., and other object of the invention is to provide the production method thereof and the uses thereof.

Furthermore, since the polyalkylene oxide-modified phospholipid of the invention has the effects of phospholipids and can be dissolved in an aqueous solution, the polyalkylene oxide-modified phospholipid can be used as a surface active agent.

The present inventions are the following polyalkylene oxide-modified phospholipid, the production method thereof, and the uses thereof.

(1) A polyalkylene oxide-modified phospholipid represented by following formula (1), wherein the content of a monoacyl phospholipid is not more than 3% by weight and the content of a base having a nitrogen atom is not more than 0.02% by weight.

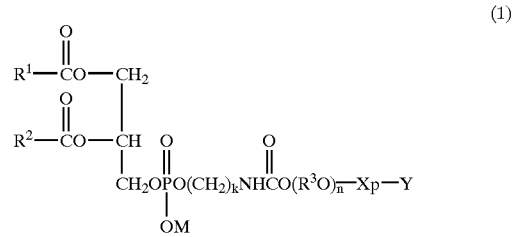

(In the formula (1), $R^1CO$ and $R^2CO$ each independently represents an acyl group having from 4 to 24 carbon atoms; k represents from 1 to 4; $R^3O$ represents an oxyalkylene group having from 2 to 4 carbon atoms; n is a mean addition mol number of the oxyalkylene group having from 2 to 4 carbon atoms, and represents a number of from 10 to 800; M represents a hydrogen atom, sodium, or potassium; X represents a divalent hydrocarbon group having from 1 to 3 carbon atoms or $-C(=O)(CH_2)_q-$ (wherein, q represents from 1 to 4); p represents 0 or 1; and when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group.).

(2) The polyalkylene oxide-modified phospholipid described in above-described (1), wherein the content of the monoacyl phospholipid is not more than 2% by weight.

(3) The polyalkylene oxide-modified phospholipid described above-described (1), wherein p is 0, Y is a methyl group, and the content of the monoacyl phospholipid is not more than 0.5% by weight.

(4) A method of producing a polyalkylene oxide-modified phospholipid, comprising following process (A).

Process (A): A process of reacting the activated material of a polyalkylene oxide compound represented by following formula (2) and a phospholipid represented by following formula (3) in an organic solvent in the presence of an alkali metal salt the aqueous solution of which shows alkalinity, which is a solid salt without containing nitrogen.

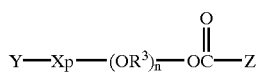

(2)

[In the formula (2), $R^3O$ represents an oxyalkylene group having from 2 to 4 carbon atoms; n is a mean addition mol number of the oxyalkylene group having from 2 to 4 carbon atoms, and represents a number of from 10 to 800; X represents a divalent hydrocarbon group having from 1 to 3 carbon atoms or $-C(=O)(CH_2)_q-$ (wherein, q represents from 1 to 4); p represents 0 or 1; and when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group; and Z represents an activating group.)

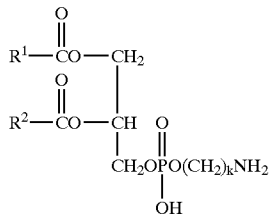

(3)

(In the formula (3), $R^1CO$ and $R^2CO$ each independently represents an acyl group having from 4 to 24 carbon atoms and k represents from 1 to 4.).

(5) The production method described in above-described (4), wherein $R^1CO$ and $R^2CO$ each is an acyl group having from 12 to 20 carbon atoms.

(6) The production method described in above-described (4) or (5), wherein p is 0 and Y is a methyl group.

(7) The production method described in above-described (4) to (6), wherein the solid salt used for the process (A) is sodium carbonate and the organic solvent is toluene or chloroform.

(8) The production method described in above-described (4) to (7), wherein the method has following process (B) after the process (A).

Process (B): A process of removing phosphatidyl ethanolamine using ethyl acetate or acetone.

(9) The production method described in above-described (4) to (8), wherein the method has following process (C) after the process (A).

Process (C): A process of carrying out a recrystallization using ethyl acetate and/or acetone as a solvent.

(10) The production method described in above-described (9), wherein in the process (C), at least one kind of the compound selected from the group consisting of aliphatic hydrocarbons having from 5 to 8 carbon atoms and ethers is further used as a solvent.

(11) The production method described in above-described (9) or (10), wherein the process (C) is carried out after the process (B).

(12) The production method described in above-described (4) to (11), wherein the method has following process (D) after the process (A).

Process (D): A process of carrying out a purification using an adsorbent.

(13) The production method described in above-described (12), wherein the adsorbent used in the process (D) is an alkaline earth metal oxide, an alkaline earth metal hydroxide, an absorbent containing aluminum or silicon, or active carbon.

(14) The production method described in above-described (12) or (13), wherein the process (D) is carried out after the process (B).

(15) The production method described in above-described (4) to (14), wherein the polyalkylene oxide-modified phospholipid is the, compound represented by following formula (1), wherein the content of a monoacyl phospholipid is not more than 3% by weight and the content of base having a nitrogen atom is not more than 0.02% by weight.

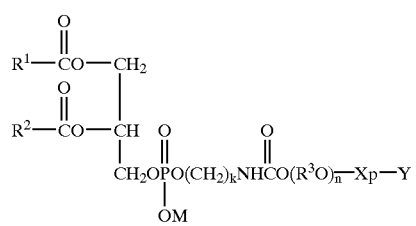

(1)

(In the formula (1), $R^1CO$ and $R^2CO$ each independently represents an acyl group having from 4 to 24 carbon atoms; k represents from 1 to 4; $R^3O$ represents an oxyalkylene group having from 2 to 4 carbon atoms; n is a mean addition mol number of the oxyalkylene group having from 2 to 4 carbon atoms, and represents a number of from 10 to 800; M represents a hydrogen atom, sodium, or potassium; X represents a divalent hydrocarbon group having from 1 to 3 carbon atoms or $-C(=O)(CH_2)_q-$ (wherein, q represents from 1 to 4); p represents 0 or 1; and when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group.).

(16) A surface active agent containing the polyalkylene oxide-modified phospholipid described in above-described (1) to (3).

(17) A liposome forming agent containing the polyalkylene oxide-modified phospholipid described in above-described (1) to (3).

(18) A liposome containing the polyalkylene oxide-modified phospholipid described in above-described (1) to (3).

(19) An amphiphilic chemical modifier of physiologically active substance containing the polyalkylene oxide-modified phospholipids described in above-described (1) to (3).

DETAILED DESCRIPTION OF THE INVENTION

In the polyalkylene oxide-modified phospholipid of the invention shown by the above-described formula (1), $R^1CO$ and $R^2CO$ each is an acyl group having from 4 to 24, and preferably from 12 to 20 carbon atoms. The acyl group is usually originated in a fatty acid. As practical examples of $R^1CO$ and $R^2CO$, there are acyl groups originated in saturated or unsaturated, straight chain or branched fatty acids such as butyric acid, isobutyric acid, caproic acid, caprylic acid, capric acid, lauric acid, myristic acid, palmitic acid, palmitoleic acid, stearic acid, isostearic acid, oleic acid, linolic acid, arachic acid, behenic acid, erucic acid, and lignoceric acid. In addition, $R^1CO$ and $R^2CO$ may be the same or different.

In the above-described formula (1), the oxyalkylene group shown by $R^3O$ is an oxyalkylene group having from 2 to 4, and preferably 2 or 3 carbon atoms. As $R^3O$, there are, for example, an oxyethylene group, an oxypropylene group, an oxytrimethylene group, and an oxybutylene group. In these groups, an oxyethylene group and an oxypropylene group are prepared, and particularly, an oxyethylene group is preferred. In the molecule, the oxyalkylene groups exist by the number of n, but the oxyalkylene group may be one kind alone or may be a combination of two or more kinds, and there is no restriction on the manner of the combination. Also, the combination may be a block form or a random form.

In the above-described formula (1), n represents a mean addition mol number of the oxyalkylene groups and is a number of from 10 to 800, and preferably from 20 to 500. When n is at least 10, in the case of using the polyalkylene oxide-modified phospholipid of the invention for a drug delivery system, the delivery effect becomes high. Also, n is not larger than 800, in the case of producing the polyalkylene oxide-modified phospholipid, the viscosity of the polyalkylene oxide compound shown by the above-described formula (2), which is a raw material, does not increased so much, whereby the workability becomes good.

In the above-described formula (1), M is a hydrogen atom, sodium, or potassium. The polyalkylene oxide-modified phospholipid of the invention shown by the formula (1) may be a mixture of them.

Sodium or potassium forming a salt with a phosphoric acid group portion is usually contained in a physiological saline buffer, which is used for the preparation of medicines, etc., and also exists in a living body. Accordingly, when the polyalkylene oxide-modified phospholipid of the invention is used for a drug delivery system, the problem of toxicity in a living body is less. When M is other metal ion than sodium or potassium, such as, for example, a divalent metal such as calcium or magnesium, the structure of associating two molecules of the phospholipid is undesirably formed.

In the above described formula (1), k is an integer of from 1 to 6, preferably from 1 to 4, and more preferably 2 to 4, further preferably 2.

In the formula (1), X is a divalent hydrocarbon group having from 1 to 3 carbon atoms or —C(=O) $(CH_2)_q$- (wherein, q represents from 1 to 4). Practical groups of the hydrocarbon group, there are —$CH_2$—, —$CH_2CH_2$—, —$(CH_2)_3$—, —$CH(CH_3)CH_2$—, etc. Also, p is 0 or 1.

In the formula (1), when p is 0, Y is a hydrogen atom or an alkyl group having from 1 to 4 carbon atoms, and is preferably the alkyl group. As the alkyl group, there are a methyl group, an ethyl group, a propyl group, a butyl group, etc. In these groups, a methyl group is preferable.

Also, when p is 1, Y is a hydrogen atom, an amino group, a carboxyl group, an aldehyde group, a glycidyl group, or a thiol group, and is preferably an amino group.

As $X_p$-Y, a methyl group, an ethyl group, a propyl group, and an aminomethyl group are preferred, and a methyl group is particularly preferred.

The polyalkylene oxide-modified phospholipid of the invention has less contents of impurities such as a monoacyl phospholipid, and a base having a nitrogen atom, which is a residue derived from a catalyst.

The content of the monoacyl phospholipid existing in the polyalkylene oxide-modified phospholipid of the invention is not more than 3% by weight, preferably not more than 2% by weight, and more preferably not more than 0.5% by weight.

Also, the content of the base having a nitrogen atom is not more than 0.02% by weight, preferably not more than 0.01% by weight, and more preferably substantially 0.

The base having a nitrogen atom is a base that is a residue derived from a catalyst such as triethylamine, and the base has at least one nitrogen atoms. As the examples of the base having nitrogen atoms, there are pyridine, triethylamine, diisopropylamine, dimethylaminopyridine, imidazole, diethylamine, diisobutylamine, tri-n-octylamine, di-2-ethylhexylamine. Of them, triethylamine is desired since it has little toxicity. In addition, the phospholipid shown by the formula (3) has a nitrogen atom but since it is neutralized in the molecule, the phospholipid does not correspond to the base having a nitrogen atom in the invention.

Since the polyalkylene oxide-modified phospholipid of the invention has less content of the monoacyl phospholipid, which is considered to have a strong biotoxicity, and has less content of impurities having nitrogen atoms, such as triethylamine, etc., the safety thereof to a living body is high.

Also, since the polyalkylene oxide-modified phospholipid of the invention contains a monovalent metal cation of a sodium ion or a potassium ion, which also exist in a living body, the safety to a living body is high.

Since the polyalkylene oxide-modified phospholipid of the invention has high safety to a living body as described above, it can be used as a surface active agent, and particularly as a surface active agent for a living body. In particular, the polyalkylene oxide-modified phospholipid can be suitably used as a surface-active agent for physiologically active substances.

The surface active agent of the invention is a surface active agent containing the polyalkylene oxide-modified phospholipid of the invention. Usually, it is desirable to use the polyalkylene oxide-modified phospholipid by compounding in an amount of from 0.01 to 30% by weight, and preferably from 0.1 to 15% by weight to the total composition such as the composition containing the surface active agent. In addition, the using amount of the surface active agent is properly selected according to the using purpose of the surface active agent and the difference of the composition.

The surface active agent of the invention may be one or two or more kinds of the polyalkylene oxide-modified phospholipids represented by formula (1), and may be used in combination with another surface active agent.

The surface active agent of the present invention can be preferably used as 1) an emulsifier emulsifying an object substance that is insoluble or difficultly soluble to water into a dispersing medium (e.g., water or buffer solution), 2) a solubilizing agent dissolving an object substance that is insoluble or difficultly soluble to water in a dispersing medium (e.g., water or buffer solution) 3) a dispersing agent dispersing an object substance that is insoluble or difficultly soluble to water in a dispersing medium (e.g., water or buffer solution), or 4) an amphiphilic chemical modifier introducing a hydrophilic or hydrophobic group into an object substance.

Also, by using the surface active agent of the invention, a solubilizing liquid, an emulsifying liquid, and a dispersion, can be obtained.

When the surface active agent of the invention is used as an emulsifier, solubilizing agent or dispersing agent, the emulsifier, solubilizing agent or dispersing agent may only contain the surface active agent of the invention, or may further contain another well-known component used in emulsifying, solubilizing or dispersing.

While the forms of the solubilizing solution or dispersing solution are not limited, the examples include a dissolving solution in which a physiologically active substance, etc., is dissolved in a dispersing medium (e.g., water or buffer solution), and a dispersing solution in which a physiologically active substance is dispersed in a dispersing medium (e.g., water or buffer solution).

While the forms of the emulsifying solution or solubilizing solution are not limited, the examples include a micelle solution formed by the surface active agent of the invention (i.e., a micelle solution containing an oleophilic physiologically active substance inside, and an emulsion solution in which dispersed particles of the surface active agent and an oleophilic physiologically active substance, etc., exist in a dispersing medium (e.g., water or buffer solution) as colloid particles or particles larger than them. An example of the micelle solution includes a polymer micelle solution (especially having a dispersion particle size of 10 to 300 nm). The emulsion solution maybe an oil-in-water (O/W) type emulsion solution in which a physiologically active substance is compounded in an oil phase, or multilayer oil-in-water (W/O/W) type emulsion solution in which a physiologically active substance is compounded in a water phase.

Since the surface active agent of the invention has a hydrophilic property originated in a polyoxyalkylene group and a hydrophobic property originated in an acyl group, the surface active agent can be used as an emulsifier or a solubilizing agent, and also is excellent in the storage stability. Furthermore, since the surface active agent of the invention is composed of a phospholipid same as a living biological cell constituting component and a polyoxyalkylene group having a low toxicity and also has a less content of monoacyl phospholipids, which sometimes is said to have some biotoxicity, the safety thereof is higher. By using the surface active agent containing such a polyalkylene oxide-modified phospholipid, for example, an emulsion or a solubilizing liquid of physiologically active substance having a high safety can be obtained.

As the object substance of the emulsification, the solubilization or dispersion, there are a biologically active substance, a fat-soluble substance, etc.

As the biologically active substance, there are, practically, enzymes, antibodies, other proteins, saccharose, lipids, glycoproteins, glycolipids, hormones, etc.

As the fat-soluble substance, there are lipids such as phospholipid, etc.; fat-soluble medicines such as taxol, etc.; higher alcohols usually used for oil phases, ester oils, triglycerol, tocopherol, and higher fatty acids.

The surface active agent of the invention can contain other known component(s) such as polyhydric alcohols (glycerol, propylene glycerol, etc.), fatty acid esters, antiseptics, antioxidants, etc., in the range of not losing the effects of the invention.

By using the polymer surface active agent containing the polyalkylene chain of the present invention, a polymer micelle solution where fine particles having a particle size of 10 to 100 nm exist can be obtained.

As the polymer micelle, the polymer surface active agent represented by formula (1) above may be used singly, or another well-known component may be further contained. As described later, a polymer surface active agent where another well-known polymer is connected to the reactive group Y described in formula (1) above. The polymer micelle contained in the polymer micelle solution can be used for solubilizing fat-soluble medicines.

To micelles using ordinary surface active agent, the polyalkylene oxide-modified phospholipid of the invention is similar to the living biological cell constituting component as described above, and further, since the polymer micelle solution prepared for containing a polyalkylene oxide chain of a high molecule has a hydration layer, the stability is high and the toxicity to a living body is low.

The polymer micelle having compounded therein from 0.05 to 2% by weight of the object substance and the surface active agent of the invention in an amount of from 0.2 to 0% by weight to the whole amounts is preferred.

The weight mean particle size of the polymer micelle obtained by a dynamic light scattering method is from 10 to 300 nm, and preferably from 20 to 100 nm.

For preparing the emulsion solution, the object substance to be emulsified with water and the surface active agent of the invention are kneaded by heating to a temperature of from 30 to 90° C., preferably from 45 to 85° C., and more preferably from 60 to 80° C., and then water or a buffer solution is gradually added to the kneaded mixture followed by mixing to obtain the emulsion solution. Another water soluble substance may be contained in the water.

For the preparation of the emulsion, the oil phase and the aqueous phase are separately prepared as described above and then, they may be mixed, or all the components may be mixed by a homogenizer, a sonicator, etc. Usually, it is better that the object substance is used in an amount of from 0.01 to 30% by weight, and preferably from 0.1 to 10% by weight to the whole amounts and the surface active agent of the invention is used in an amount of from 0.1 to 40% by weight, and preferably from 0.5 to 10% by weight to the whole amounts.

For the preparation of the solubilizing liquid, the object substance to be dissolved in water and the surface active agent of the invention are mixed usually at room temperature, and preferably at a temperature of from 30 to 45° C., and then water or buffer solution is gradually added to the mixture followed by mixing to obtain a homogeneous solubilizing liquid. In this case, an aqueous phase containing another water-soluble substance may be used as the water. For mixing, a homogenizer, a sonicator, etc., is used. Usually, it is better that the object substance is used in an amount of from 0.01 to 10% by weight, and preferably from 0.1 to 5% by weight to the whole amounts and the surface active agent of the invention is used in an amount of from 0.1 to 30% by weight, and preferably from 1 to 10% by weight to the whole amounts.

When Y of the above-described formula (1) in the invention is a reactive functional group, the surface active agent of the invention can be used as the amphiphilic chemical modifier of a physiologically active substance.

The amphiphilic chemical modifier may contain one kind or two or more kinds of the surface active agents of the invention, and further may contain other known component(s) used for the chemical modification of physiologically active substances.

There is no particular restriction on the physiologically active substance used for the chemical modification if the substance has a functional group such as an amino group, a carboxyl group, a hydroxyl group, a thiol group, etc. For example, there are enzymes, antibodies, other oligo and polypeptides, proteins, saccharose, lipids, glycoproteins, glycolipids, hormones, etc.

When the surface active agent of the invention is used as the amphiphilic chemical modifier of a physiologically active substance, Y of the formula (1) is preferably an amino group, a carboxyl group, an aldehyde group, or a thiol group. When the surface active agent of the invention has an amino group, a carboxyl group, an aldehyde group, or a thiol group, the group can be easily reacted with the functional group existing in the physiologically active substance. For example, when Y is a carboxyl group, by forming a CONH bond with the amino group in the physiologically active substance, the polyalkylene oxide-modified phospholipid skeleton can be introduced into the physiologically active substance.

Also, the amphiphilic chemical modifier of a physiologically active substance can be used as a solubilizing liquid, an emulsion, a dispersion, or a polymer micelle solution. For example, when a fat-soluble medicine is prepared using the polyalkylene oxide-modified phospholipid of the invention by the above method to form a polymer micelle solution, and further when Y is a reactive functional group such as a carboxyl group, etc., by reacting with the amino group of an antibody protein to bond thereto, a polymer micelle preparation capable of being administered to the target site can be obtained.

When the physiologically active substance chemically modified using the amphiphilic chemical modifier of the invention is used as a liposome component, the physiologically active substance can exist on the surface of the liposome. For example, when the physiologically active substance is a protein of an antibody, the physiologically active substance can be used as the ligand of a target cell, whereby the liposome can be concentrically transported to the target cell.

In the case of using as the amphiphilic chemical modifier of a physiologically active substance, the amphiphilic chemical modifier can be used as a solubilizing liquid, an emulsion, a dispersion, a polymer micelle solution, and a liposome solution.

The liposome of the invention is a liposome composed of a liposome-forming agent containing the polyalkylene oxide-modified phospholipid of the invention. Also, the liposome of the invention may contain other known liposome used for forming a liposome film as a component.

Usually, it is desirable to use the polyalkylene oxide-modified phospholipid of the invention in a compounded amount of from 0.002 to 0.2 mol, and preferably from 0.01 to 0.1 mol to one mol of a phospholipid. It is preferred that the polyalkylene oxide-modified phospholipid of the invention is used in a compounded amount of from 0.1 to 20% by weight to the whole composition of the liposome.

The liposome of the invention obtained by the liposome-forming agent can be produced using the polyalkylene oxide-modified phospholipid of the invention and other lipid.

As other lipid, there are a phospholipid, sterols, and a saturated or unsaturated compound having an acyl group and from 8 to 22 carbon atoms.

Also, other lipid may be a phospholipid containing phosphatidyl choline singly or a mixture thereof and other lipid.

The phospholipid means a glycerophospholipid, a sphingophospholipid, and a glyceroglycolipid, and the sterols mean cholesterol, dihydrocholesterol, ergosterol, and lanosterol, etc.

As the glycerophospholipid, there are phosphatidyl choline having an a saturated or unsaturated and straight chain or branched acyl group having from 4 to 24, and preferably from 12 to 20 carbon atoms, phosphatidyl ethanolamine, phosphatidyl glycerol, phosphatidyl inositol, and phosphatidyl serine. Also, mixed lipids originated in a natural product, such as egg yolk lecithin and soybean lecithin can be used.

As the acyl group having from 4 to 24 carbon atoms, there are the acyl groups originated in caprylic acid, capric acid, lauric acid, myristic acid, palmitic acid, palmitoleic acid, stearic acid, isostearic acid, oleic acid, linolic acid, arachic acid, behenic acid, etc.

Other lipid may be composed of the mixed lipids of the composition ratio shown below.

That is, phosphatidyl choline/cholesterol/phosphatidyl glycerol is 20–90/10–60/2–40 mol %, and preferably 30–60/20–50/15–25 mol %.

The liposome obtained from the liposome-forming agent of the invention can be produced by known methods.

For example, as a general Bangahm method, a lipid as a raw material is dissolved in an organic solvent capable of dissolving the lipid, the solvent is removed using an evaporator, etc., to form a thin lipid film, after hydrating and emulsifying at a temperature higher than the phase transition, a liposome solution is obtained by a ultrasonic treatment. Also, the above-described lipid as the raw material is hydrated, and after emulsifying using a homogenizer, etc., at a temperature higher than the phase transition, a liposome solution is obtained by a method of press-filtering using a membrane of polycarbonate (Hope M. J., et al., "Biochimica et Biophysica Acta, 812, 55(1985)). Also, the liposome obtained may be controlled to proper particle sizes even when it is a multilamella liposome is a single lamella liposome. A single lamella liposome having particle sizes of from 60 to 300 nm, and preferably from 90 to 200 nm is preferred.

Since the liposome-forming agent of the invention contains the polyalkylene oxide-modified phospholipid of the invention, the liposome solution obtained using the liposome-forming agent is excellent in the storage stability, has less content of a monoacyl phospholipid having a strong biotoxicity, for example, has less contents of impurities containing nitrogen, such as triethylamine, etc., and furthermore, the liposome solution is safe for a living body. Accordingly, by using the liposome-forming agent of the invention, a liposome, which can be utilized as a drug delivery system having a high safety, can be obtained.

As the reasons that the liposome solution prepared using the liposome-forming agent of the invention is excellent in the storage stability, the following matters are consumed. That is, since a monoacyl phospholipid has a low hydrophobic property as compared with a diacyl phospholipid, the former is liable to be released from the surface of a liposome. Accordingly, since a related art liposome having a high content of a monoacyl phospholipid is released from the surface of the liposome to reduce the hydration layer on the surface of the liposome, the liposome particles are liable to be aggregated to cause a phase separation and the liposome become unstable. On the other hand, since the polyalkylene oxide-modified phospholipid of the invention has less content of a monoacyl phospholipid, the phospholipid is hard to released from the surface of the liposome, whereby the liposome solution becomes excellent in the storage stability.

In the synthesis method of the polyalkylene oxide-modified phospholipid of the invention, a base containing nitrogen, such as triethylamine is not used as a catalyst. Accordingly, in the polyalkylene oxide-modified phospholipid, au unfavorable base does not remain, and the polyalkylene oxide-modified phospholipid, which is safety and has a high purity, can be obtained.

The polyalkylene oxide-modified phospholipid of the invention can be easily produced by following process (A).

Process (A): A process of reacting the activated material of a polyalkylene oxide compound shown by the above-described formula (2) and a phospholipid shown by the above-described formula (3) in an organic solvent in the presence of an alkali metal salt the aqueous solution of which shows alkalinity, which is a solid salt without containing nitrogen.

In the polyalkylene oxide compound shown by the formula (2) and the phospholipid shown by the formula (3), $R^1CO$, $R^2CO$, $R^3O$, k, n, X, p, and Y are same as those explained in the above-described formula (1).

In the polyalkylene oxide compound shown by the formula (2), Z is an activating group, that is a group imparting a reactive activity to the polyalkylene oxide compound with the phospholipid show by the formula (3), and includes an electron-attracting group and other groups. As such groups, there are, practically, an imidazole group, a 4-nitrophenyloxy group, a benzotriazole group, chlorine, a methoxy group, ethoxy group, a propyloxy group, a carbonyloxy-N-2-pyrrolidinone group, a carbonyl-2-oxypyrimidine group, an N-succinimidyloxy group, a pentafluorobenzoyl group, etc. In these groups, an imidazole group, a 4-nitrophenyloxy group, a benzotriazole group, chlorine, and an N-succinimidyloxy group, are preferred, and a 4-nitrophenyloxy group is particularly preferred.

The phospholipid shown by the above-described formula (3) may be a natural phospholipid or a synthetic phospholipid. As the practical examples, there are natural or synthetic phosphatidyl ethanolamines such as a soybean phosphatidyl ethanolamine, a soybean hydrogenated phosphatidyl ethanolamine, an egg yolk phosphatidyl ethanolamine, an egg yolk hydrogenated phosphatidyl ethanolamine. As the phospholipid shown by the above-described formula (3), the phosphatidyl ethanolamine, wherein k of the formula (3) is 2, is preferred.

The solid salt used in the process (A) is an alkali metal salt, the aqueous solution of which shows an alkalinity, and is a solid salt without containing nitrogen. As the solid salt, a compound capable of bonding the activated product of the polyalkylene oxide compound shown by the formula (2) to the amino group of the phospholipid shown by the formula (3) can be used without any restriction.

Practically, the solid salt is a solid salt that when the aqueous solution formed by dissolving in water, the pH shows an alkalinity. The pH is preferably from 7.1 to 13, and more preferably from 7.1 to 11. As the solid salt, a solid salt containing sodium or potassium is preferred. As the solid salt, there are carbonates, phosphates, acetates, etc. Practically, there are sodium carbonate, potassium carbonate, sodium hydrogencarbonate, potassium hydrogencarbonate, sodium acetate, potassium acetate, etc. In these salts, sodium hydrogencarbonate and sodium carbonate are preferred, and sodium carbonate is particularly preferred.

The using amount of the solid salt is preferably from 0.1 to 1000 mol times the amount of the polyalkylene oxide compound. When the using amount is lower than 1000 mol times, stirring is preferably easy. It is particularly preferred that the using amount of the solid salt is from 1 to 500 mol times.

As the charging amounts of the activated product of the polyalkylene oxide compound shown by the formula (2), which is used, and the phospholipid of the formula (3), it is desirable that the mol ratio thereof is as near as 1:1, but it is more desirable to establish such that the phospholipid becomes excessive. Practically, it is desirable that the mol ratio of the activated product of the polyalkylene oxide compound to the phospholipid is from 1:1 to 1:5, preferably from 1:1.1 to 1:2.

When the phospholipid becomes excessive, the excessive phospholipid can be removed from the product in the process as described below. On the other hand, when the polyalkylene oxide compound becomes excessive, after the reaction is finished, the unreacted polyalkylene oxide remains. In this case, when the molecular weight of the polyalkylene oxide compound is from about 100 to about 3000, the remaining polyalkylene oxide compound can be removed by the method of recrystallization, crystallization, etc. However, in this case, it sometimes happens that the yield of the polyalkylene oxide-modified phospholipid is lowered. On the other hand, when the molecular weight of the polyalkylene oxide compound is at least about 3000, it is frequently difficult to remove the remaining polyalkylene oxide compound. Since in this case, it is difficult to obtain the polyalkylene oxide-modified phospholipid of high purity, the above molar ratio is preferable.

In the production method of the reaction, the polyalkylene oxide compound shown by the above-described formula (2) can be reacted with the phospholipid shown by the above-described formula (3) in the presence of the above-described solid salt as described above. However, as the case may be, the polyalkylene oxide-modified phospholipid of the invention can be also obtained by reacting the activated product of a phospholipid and the polyalkylene oxide compound.

As the organic solvent used for the reaction of the process (A), any organic solvents having no functional group such as a hydroxyl group, etc., can be used without particular restriction. As the examples of the organic solvent, there are aprotic solvents like ethyl acetate, dichloromethane, chloroform, benzene, and toluene. In these solvents, toluene and chloroform are preferred. Organic solvents each having a hydroxyl group, such as ethanol, etc., are undesirable since the organic solvent causes a reaction with the terminal active group of the activated product of the polyalkylene oxide compound shown by the formula (2). There is no problem in the reactivity of dichloromethane, etc., but since such a solvent has a low boiling point, it is undesirable for working.

It is desirable that the reaction temperature of the reaction of the process (A) is from 30 to 90° C., and preferably from 40 to 80° C. It is also desirable that the reaction time is at least one hour, and preferably from 2 to 10 hours.

By reacting the polyalkylene oxide compound shown by the formula (2) and the phospholipid shown by the formula (3), the polyalkylene oxide-modified phospholipid of the invention shown by the above-described formula (1) is obtained.

In addition, in the process (A), when the terminal of the polyalkylene oxide compound shown by the formula (2) is an amino group, a carboxyl group, or a thiol group, and particularly is an amino group, it is preferred that the polyalkylene oxide compound is used for the reaction by protecting the terminal group. For example, it is preferred that in the case of an amino group, the amino group is protected with a tert-butoxycarbonyl group, in the case of a carboxyl group, the group is protected by esterified with a methyl group, etc., and in the case of a thiol group, the group is protected with an S-t-butyl sulfide group.

After filtering off solid salts from the reaction liquid obtained in the process (A), by a method of concentrating the filtrate or crystallizing the filtrate by adding it into a bad solvent, the polyalkylene oxide-modified phospholipid of the invention shown by the formula (1) can be obtained at a high purity and at a high yield. There is no particular restriction on the filter used for the filtration if the filter can remove the impurities in the liquid to be treated, and usually, various filters such as papers, glasses, etc., having a retained particle fine particle sizes of from 1 to 10 $\mu$m and having a solvent resistance can be used. There is no particular restriction on the filtration method, and, for example, a vacuum filtration, a press filtration, a centrifugal filtration, etc., can be used.

Also, by controlling the pH of the filtrate obtained in the process (A), the polyalkylene oxide-modified phospholipid obtained can be changed to a hydrogen type wherein M of the phosphoric acid group portion in the above formula (1) is hydrogen, or an alkali salt type wherein M is sodium or potassium.

By applying the processes (B) to (D) as described below to the polyalkylene oxide-modified phospholipid obtained or the solution of the process (A) containing the polyalkylene oxide-modified phospholipid obtained, the polyalkylene oxide-modified phospholipid having a higher purity can be obtained. In addition, it is preferred that the processes (B) to (D) are carried out after removing solid salts from the reaction liquid of the process (A) by the filtration as described above.

In the process (B), the excessive phospholipid existing as impurities at dissolving the crystals obtained in the process (A) in an organic solvent is removed.

As the organic solvent used, a solvent, which dissolves the polyalkylene oxide-modified phospholipid as the objective product but does not dissolve excessively existing phospholipid, or a solvent having a low solubility for the phospholipid is preferred. Practically, as the organic solvent, ethyl acetate or acetone is preferred, and acetone is particularly preferred.

The dissolving temperature of the process (B) is preferably from 0 to 80° C., and particularly preferred from 20 to 70° C. The amount of the organic solvent is from 1 to 100 weight times, and preferably from 2 to 50 weight times the weight of the crystals.

After filtering off impurities from the solution of the process (B), by a method of concentrating the filtrate or crystallizing by adding the filtrate into a bad solvent (poor solvent), the polyalkylene oxide-modified phospholipid of the invention shown by the formula (1) can be obtained at a high purity and at a high yield.

In addition, by only cooling the filtrate obtained, the crystallization can be carried out, but according to the kind of the solvent, the polyalkylene oxide-modified phospholipid shown by the formula (1) is not sufficiently crystallized and remains in the solution, whereby there is a possibility of lowering the yield.

Also, the polyalkylene oxide-modified phospholipid may be crystallized by removing the organic solvent by distillation, etc. In the case of distilling off the organic solvent, it is preferred to carry out the distillation at a temperature of not higher than 80° C. and under a reduced pressure. When the distillation temperature of the organic solvent exceeds 80° C., there is a possibility of causing an undesirable side-reaction such as the decomposition of the polyalkylene oxide-modified phospholipid shown by the formula (1).

Also, as described above, by controlling the pH of the filtrate obtained in the process (B), the polyalkylene oxide-modified phospholipid can be converted to a hydrogen type or an alkali salt type.

The process (B) may be carried out after the process (A), or may be carried out before the process (C) or the process (D) described below, or further may be carried out after the process (C) and/or the process (D).

The polyalkylene oxide-modified phospholipid of the invention can be obtained from the crystal, as it is, obtained in the process (B), and further the crystal obtained may be subjected to purification.

In the method of the invention, it is preferred that by carrying out the process (C) and/or the process (D) described below after the process (A), a compound originated in Z formed from the reaction activity imparting group Z in the activated product of the polyalkylene oxide compound shown by the formula (2), which is the raw material in the process (A), is removed. Each of the processes (C) and (D) may be carried out after the process (A), before or after the process (B), and each one of the processes (C) and (D) may be carried out first. However, it is preferred that the processes (C) and (D) are carried out after the process (B) and also it is preferred that the process (D) is carried out after the process (C).

In the process (C), the crystals obtained in the process (A) are dissolved and by crystallizing the crystals of the polyalkylene oxide-modified phospholipid by cooling or by adding a bad solvent, compounds originated in Z are removed to carry out the purification.

As the solvent used in the process (C), a solvent, which dissolve the crystals obtained in the process (A) and crystallizes the crystals of the polyalkylene oxide-modified phospholipid by cooling, or a solvent which can crystallize the polyalkylene oxide modified phospholipid by adding a bad solvent is preferred. A solvent wherein at crystallizing the crystals, the polyalkylene oxide-modified phospholipid, which is the objective product, is crystallized, and compounds originated in Z are in the dissolved state is particularly preferred.

The amount of the solvent used in the process (C) is from 1 to 100 weight times, and preferably from 2 to 50 weight times the weight of the crystals.

In the process (C), after recrystallizing, cooling is carried out or using a bad solvent, a crystallization is carried out. Preferably, by cooling at a temperature of 10° C. or lower, the crystallization is sufficiently carried out and the crystals are obtained at a good yield.

The crystallization may be carried out by distilled off the solvent. In the case of distilling off the solvent, it is desirable to carried out the distillation at a temperature of not higher than 80° C. under a reduced pressure. When the distillation temperature of the organic solvent exceeds 80° C., there is a possibility of causing an undesirable side-reaction such as the decomposition of the polyalkylene oxide-modified phospholipid shown by the formula (1).

As the practical method of the process (C), there are the following methods.

(i) After dissolving in at least one kind of a solvent selected from ethyl acetate and acetone, the crystals of the polyalkylene oxide-modified phospholipid are crystallized by cooling.

(ii) After dissolving in at least one kind of a solvent selected from ethyl acetate and acetone, the crystals of the polyalkylene oxide-modified phospholipid are crystallized using ether or an aliphatic hydrocarbon having from 5 to 8 carbon atoms.

(iii) After dissolving in a combined solvent of at least one kind of a solvent selected from ethyl acetate and acetone, and ether or a solvent of an aliphatic hydrocarbon having from 5 to 8 carbon atoms, the crystals of the polyalkylene oxide-modified phospholipid are crystallized by cooling.

In the methods described above, the method (i) wherein after dissolving using ethyl acetate and the crystals of the polyalkylene oxide-modified phospholipid are crystallized by cooling is preferred.

There is no particular restriction on the above-described aliphatic hydrocarbon having from 5 to 8 carbon atoms used in the process (C). For example, there are pentane, isopentane, neopentane, hexane, isohexane, 3-methylpentane, neohexane, 2,3-dimethylbutane, heptane, 2-methylhexane, 3-methylhexane, 3-ethylpentane, 2,2-dimethylpentane, 2,3-dimethylpentane, 3,3-dimethylpentane, 2,3,3-trimethylbutane, octane, 2-methylheptane, 3-methylheptane, 4-methylheptane, 3-ethylhexane, 2,2-dimethylhexane, 2,3-dimethylhexane, 2,4-dimethylhexane, 2,5-dimethylhexane, 3,3-dimethylhexane, 3,4-dimethylhexane, 2-methyl-3-ethylpentane, 3-methyl-3-ethylpentane, 2,2,3-trimethylpentane, 2,2,4-trimethylpentane, and 2,2,3,3-tetramethylbutane. In these aliphatic hydrocarbons, hexane and heptane are preferred.

At carrying out the process (C), when it is intended to further increase the purity, by repeating several times the process (c) similarly, the polyalkylene oxide-modified phospholipid having a further excellent purity can be obtained.

The crystals obtained by the process (C) Can be used as they are for obtaining the polyalkylene oxide-modified phospholipid or may be subjected to further other purification process.

In the process (D), after dissolving the crystals in a solvent, by a method of adding an adsorbent followed by stirring, etc., compounds originated in Z are removed. In addition, the process (D) can be carried out using a filtrate formed by filtering the reaction liquid obtained in the process (A).

As the solvent used in the process (D), ethyl acetate, chloroform, toluene, acetone, etc., are preferably used, and ethyl acetate is particularly preferred.

It is desirable that the temperature of treating using an adsorbent is from 10 to 85° C., and preferably from 40 to 70° C. and the time is from 10 minutes to 5 hours, and preferably from 30 minutes to 3 hours.

The crystals obtained in the process (A) may be dissolved by heating and subjected to the treatment with an adsorbent but since the case of not dissolving the crystals at the above-described temperature and the case that the viscosity of the solution is high frequently occur, it is preferred to treat the solution of the crystals by diluting with the solvent dissolving the polyalkylene oxide-modified phospholipid of the invention, such as ethyl acetate, etc. When the treating temperature is lower than 10° C., it sometime occurs that the polyalkylene oxide-modified phospholipid is crystallized, as well as in the case of removing the adsorbent, the polyalkylene oxide-modified phospholipid is removed together to lower the yield thereof, which is undesirable. Also, when the temperature exceeds 85° C., in the case of existing a fine amount of water, there is a possibility that the hydrolysis, etc., of the polyalkylene oxide-modified phospholipid occurs during the treatment with the adsorbent.

It is desirable that the using amount of the adsorbent is from 0.1 to 200 parts by weight, and preferably from 1 to 50 parts by weight to 100 parts by weight of the crystals to be treated. When the amount of the adsorbent is from 0.1 to 200 parts by weight, the compounds originated in Z can be sufficiently removed with a good efficiency.

In the process (D), the adsorbent treatment is carried out, and after removing the adsorbent by a method of filtration, etc., by carrying out cooling or using a bad solvent, the crystallization can be carried out. Preferably, by cooling to a temperature of 10° C. or lower, the crystallization is sufficiently carried out and the crystals are obtained with a good yield.

After removing the adsorbent, the crystallization may be carried out by distilling off the solvent, and in the case of distilling off the solvent, it is desirable to carry out the distillation at a temperature of not higher than 80° C. and under a reduced pressure. When the distilling off temperature of the organic solvent exceeds 80° C., there is a possibility of causing an undesirable side-reaction such as the decomposition of the acyl group of the polyalkylene oxide-modified phospholipid.

As the absorbent used in the process (D), there are absorbents containing an alkaline earth metal oxide, an alkaline earth metal hydroxide, aluminum or silicon, and active carbon, and, for example there are adsorbents containing aluminum hydroxide, aluminum oxide, magnesium oxide, magnesium hydroxide, silicon oxide, etc., and active carbon. As commercially available products of the adsorbents containing these compounds, there are Kyoward 200, Kyoward 300, Kyoward 500, Kyoward 600, Kyoward 700, Kyoward 1000, and Kyoward 2000 (trade names, manufactured by Kyowa Kagaku Kogyo K. K.), Tomix-AD300, Tomix-AD500, and Tomix-AD700 (trade names, manufactured by Tomita Seiyaku K. K.), etc. The absorbents can be used singly or a combination of two or more kinds.

The crystals obtained in the process (D) can be used as the absorbents containing of the invention as they are, or the filtrate obtained in the process (D) is not crystallized and can be more purified by applying an adsorbent treatment.

By the method as described above, the high-pure polyalkylene oxide-modified phospholipid having less content of monoacyl phospholipids as a by-product and less content of impurities like a base having a nitrogen atom, which is remained in a final product by a conventional production method and is difficult to completely separate from the final product, and can be easily produced with a high yield.

The polyalkylene oxide-modified phospholipid of the invention is novel and useful. Since the polyalkylene oxide-modified phospholipid of the invention is the high-pure polyalkylene oxide-modified phospholipid having less contents of monoacyl phospholipid and impurities having a nitrogen atom and having a high safety to a living body, it can be suitably utilized as a surface active agent, especially an emulsifier, a solubilizing agent, polymer micelle-forming agent, a dispersant, a liposome-forming agent, an amphiphilic chemical modifier etc. Of them, a liposome-forming agent is preferably used.

In the production method of the invention, the polyalkylene oxide compound shown by the above-described formula (2) is reacted with the phospholipid shown by the above-described formula (3) in an organic solvent in the presence of a solid salt without containing nitrogen, which is an alkali metal salt showing an alkalinity when the salt is dissolved in water. Accordingly, the polyalkylene oxide-modified phospholipid having less content of a monoacyl phospholipid and having less content of impurities having a nitrogen atom can be produced at a high purity.

EXAMPLES

Then, the examples of the invention are explained. In the examples, % is, unless otherwise indicated, is % by weight.

Example 1

(1) Synthesis of monomethyloxyethylenecarbamyl distearoylphosphatidyl ethanolamine (compound of formula (4) shown below):

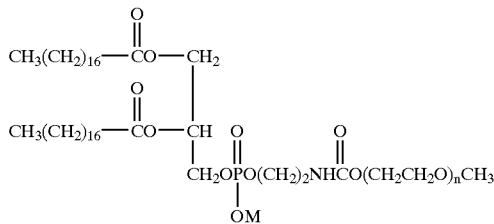

(4)

(n=45, M=H, Na)

To polyoxyethylene monomethylether (molecular weight 2000, 20 g, 10 mmol) was added toluene (80 ml), the mixture was refluxed at 110° C., and dehydrated for one hour. After cooling to 50° C., 1,1'-carbonyl diimidazole (1.95 g, 12 mmol) was added thereto and the reaction was carried out for 2 hours, so as to obtain an activated body. Then, sodium carbonate (42.4 g, 400 mmol) and distearoylphosphatidyl ethanolamine (11.22 g, 15 mmol) were added, and after raising the temperature to 65° C., the reaction was carried out for 8 hours.

After filtering off sodium carbonate, hexane (300 ml) was added to the filtrate to cause crystallization. After collecting the crystals by filtration (One gram of the crystal was sampled and the sample was defined as sample (1) in the process (A), and hereinafter, samples similarly samples were defined as samples (2) to (6)), acetone (80 ml) was added to the crystals followed by increasing the temperature to 50° C. The reaction mixture was filtered by a glass filter to remove undissolved matters. By adding hexane (160 ml) to the filtrate, the product was crystallized and the mixture was cooled to 5° C. Thereafter, the crystals were collected by filtration (sample (2) in the process (B)).

To the crystals was added ethyl acetate (400 ml) followed by dissolving the crystals at 65° C., and after stirring for 30 minutes, the solution was cooled to 5° C. The crystals thus crystallized were collected by filtration (sample (3) in the process (C)). Similarly, the process with ethyl acetate was further repeated once (sample (4) in the process (C)).

The crystals were dissolved in ethyl acetate (400 ml), Kyoward #2000 (5 g) and Kyoward #700 (0.8 g) were added as adsorbents, and the mixture was stirred for one hour at 65° C. After filtering off the adsorbents, the filtrate was cooled to 5° C. to cause crystallization (sample (5)). After collecting the crystals by filtering, the adsorbent treatment was further repeated once. After washing the crystals with hexane (200 ml), the crystals were collected by filtration, and dried to obtain 14.6 g (yield 52.2%) of the desired compound (sample (6) in the process (D)). The purity of the finally obtained crystals was 98.4%.

The analysis of the product in each stage was carried out by a thin-layer chromatography (TLC) using a silica gel plate. As the developing solvent, a mixed solvent of chloroform and methanol of a mixing ratio of 85:15 by volume ratio was used, and the sample was colored with a iodine vapor, whereby the determination of the contained substance was carried out by comparing with a standard substance having a known amount.

Similarly, using a mixed solvent of chloroform, methanol, water, and an aqueous ammonia at a mixing ratio of 65:25:4:0.1 as the developing solvent, TLC was carried out.

By the former, as impurities the determination of a lyso form, a free phospholipid, a free polyethylene glycol derivative, and triethylamine can be possible and by the latter, the determination of the triethylamine amount in the triethylamine salt of the phosphoric acid portion in the polyalkylene oxide-modified phospholipid is possible.

The results of the purities obtained by these methods are shown in Table 1 below.

On the other hand, for measuring the amounts of the compounds originated in Z contained in the substance in each process, the analysis was carried out about each of the samples (1) to (6). After drying the samples (1) to (6) under a reduced pressure, 50 mg of each sample was placed in a sample tube, ethanol was added to make the whole amount 5 g and the sample was dissolved in ethanol. By a spectrophotometer, the absorbance of 248 nm originated in 1,1'-carbonyl diimidazole (CDI) was measured. From the measured value of each sample, the removing ratio of the compound originated in 1,1'-carbonyl imidazole was obtained in each process, and the results obtained are shown in Table 2.

From the results of Table 2, it has been confirmed that in each process, the compound originated in Z is reduced and the polyalkylene oxide-modified phospholipid is purified. In addition, the polyalkylene oxide-modified phospholipid finally contains the compound originated in 1,1'carbonyl diimidazole in an amount of about 0.02%, but the value of the extent is the value, which can be ignored as the content of impurities.

Example 2

(2) Synthesis of monomethyl polyoxyethylenecarbamyl distearoylphosphatidyl ethanolamine (the compound shown by following formula (5))

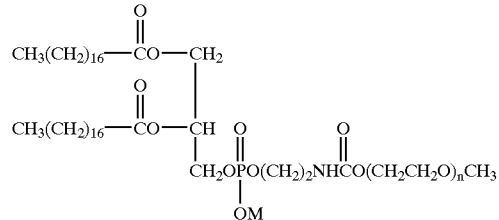

(5)

(n=45, M=H, Na)

In a reaction vessel were placed polyoxyethylene monoethylether (molecular weight 2000, 50 g, 25 mmol), sodium carbonate (53.0 g, 150 mmol), and toluene (200 ml) and the mixture was heated to 75° C. Then, p-nitrophenyl chloroformate (12.6 g, 62.5 mmol) was added to the mixture and the reaction was carried out for 9 hours, so as to obtain an activated body. After cooling to 65° C., distearoylphosphatidyl ethanolamine (28.1 g, 37.5 mmol) was added and the reaction was carried out for 7.5 hours.

After filtering off sodium carbonate, hexane (500 ml) was added to the filtrate, and after cooling to 5° C., the crystals deposited were collected by filtration. To the crystals was added acetone (200 ml), and after heating to 50° C., the mixture was filtered with a glass filter to remove undissolved matters (process (B)).

After adding hexane (500 ml) to the filtrate, the mixture was cooled to 5° C. After collecting the crystals deposited by filtration, the crystals were supplied to the process (C). In the process (C), ethyl acetate (750 ml) was added to dissolve the crystals at 65° C. and after stirring for 30 minutes, the solution was cooled to 5° C., and the crystals deposited were collected by filtration. Similarly, the process (C) using ethyl acetate was further repeated once.

The crystals were dissolved in ethyl acetate (750 ml), Kyoward #2000 (12 g) and Kyoward #700 (1 g) were added as adsorbents, and the mixture was stirred for one hour at 60° C. After filtering off the adsorbents, the filtrate was cooled to 5° C., and the crystals deposited were collected by filtration (process (D)). Similarly, the treatment with the adsorbents of the process (D) was repeated twice.

After washing the crystals with hexane (300 ml), the crystals were collected by filtration and dried to obtain 38.2 g (yield 54.6%) of the desired compound. The purity was 99.5%. The result of the purity is shown in Table 1.

Example 3

(3) Synthesis of monomethyl polyoxyethylenecarbamyl distearoylphosphatidyl ethanolamine (the compound shown by following formula (6))

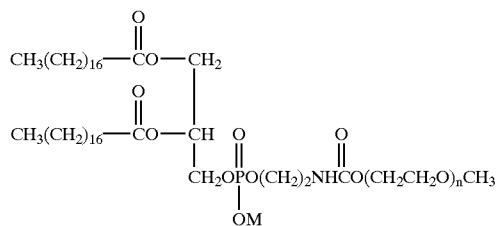

(n=113, M=H, Na)

In a reaction vessel were placed polyoxyethylene monomethylether (molecular weight 5000, 20 g, 4 mmol), sodium carbonate (17.0 g, 160 mmol), and toluene (75 ml), and the mixture was heated to 75° C. Then, p-nitrophenyl chloroformate (2.7 g, 13.2 mmol) was added and the reaction was carried out for 9 hours so as to obtain an activated. After cooling to 65° C., distearoylphosphatidyl ethanolamine (4.5 g, 6 mmol), and the reaction was carried out for 6 hours.

After filtering off sodium carbonate, hexane (200 ml) was added to the filtrate, and the crystals deposited were collected by filtration. To the crystals was added acetone (150 ml), and after heating the mixture to 50° C., the mixture was filtered with a glass filter to remove undissolved matters (process (B)).

Then, by adding hexane (300 ml), crystals were crystallized. After collecting the crystals by filtration, ethyl acetate (400 ml) was added to the crystals obtained followed by dissolving the crystals, after stirring the solution for 30 minutes, the solution was cooled to 5° C., and the crystals deposited were collected by filtration (process (C)). Furthermore, the process (C) using ethyl acetate was repeated twice.

After dissolving the crystals in ethyl acetate (360 ml), Kyoward #2000 (4 g) and Kyoward #700 (0.2 g) were added as adsorbents, and the mixture was stirred for one hour at 65° C. After filtering off the adsorbents by filtration, the filtrate was cooled to 5° C., and the crystals deposited were collected by filtration (process (D) Similarly, the treatment with the adsorbents of the process (D) was repeated twice.

After washing the crystals with hexane (90 ml), the crystals were collected by filtration and dried to obtain 15.2 g (yield 65.4%) of the desired compound. The purity was 98.4%. The result of the purity is shown in Table 1.

Example 4

(4) Synthesis of monomethyl polyoxyethylenecarbamyl dipalmitoylphosphatidyl ethanolamine (the compound shown by formula (7)):

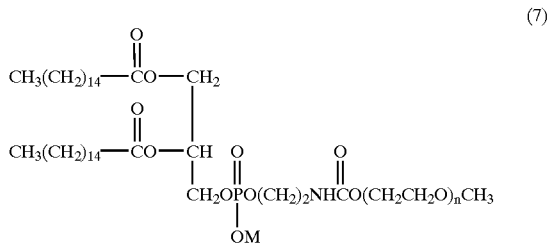

(n=113, M=H, Na)

In a reaction vessel were placed polyoxyethylene monomethylether (molecular weight 5000, 20 g, 4 mmol), sodium carbonate (33.9 g, 320 mmol), and toluene (75 ml), and the mixture was heated to 75° C. Then, p-nitrophenyl chloroformate (2.82 g, 14 mmol) was added, and the reaction was carried out for 9 hours so as to obtain an activated body. After cooling to 65° C., dipalmitoylphosphatidyl ethanolamine (3.2 g, 6 mmol) was added and the reaction was carried out for 5 hours. After filtering off sodium carbonate by filtration, hexane (200 ml) was added to the filtrate and the mixture was cooled to 5° C. The crystals deposited were collected by filtration. To the crystals was added acetone (150 ml), and after heating to 5° C., undissolved matters were removed by a glass filter (process (B)).

By adding hexane (300 ml) to the filtrate, crystals were crystallized. After collecting the crystals by filtration, to the crystals obtained was added ethyl acetate (400 ml) followed by dissolving the crystals at 65° C., and the mixture was stirred for 30 minutes. After cooling to 5° C., the crystals deposited were collected by filtration (process (C)). Furthermore the process (C) using ethyl acetate was repeated twice.

The crystals were dissolved in ethyl acetate (360 ml) and Kyoward #2000 (4 g) and Kyoward #700 (0.2 g) were added as adsorbents. After filtered off the adsorbents, the mixture was cooled to 5° C. and the crystals deposited were collected by filtration (process (D)). Similarly, the treatment with the adsorbents of the process (D) was repeated twice.

After washing the crystals with hexane (90 ml), the crystals were collected by filtration and dried to obtain 15.2 g (yield 65.6%). The purity was 98.5%. The result of the purity is shown in Table 1.

Comparative Example 1

(1) Synthesis of pyridyldithiopropionoylamino polyethylene glycol distearoylphosphatidyl ethanolamine:

After dissolving pyridylditiopropionoyl polyethylene glycol succinimidyl carbonate (1 g, 0.42 mmol) in chloroform (10 ml), distearoylphosphatidyl ethanolamine (0.36 g, 0.44 mmol) and then triethylamine (0.33 ml, 2.37 mmol) were added to the solution. The reaction mixture was stirred for 10 minutes at 40° C. After concentrating the reaction liquid by an evaporator under a reduced pressure, acetonitrile (50 ml) was added and the solution was cooled overnight at 4° C. Then, a centrifugal separation was carried out and a transparent solution was separated. After concentrating the solution by an evaporator, the crystals obtained were dried. The amount obtained was 1.15 g and the yield was 90.8%. The result of the purity is shown in Table 3.

About the free triethylamine content and the free salt content shown in Table 3, in the point of a thin-layer chromatography (TLC), the determination is possible until 5% but the determination is impossible about the value more than 5%, and thus, the content exceeding 5% is shown by >5.

Comparative Example 2

(2) Synthesis of monomethyl polyoxyethylenecarbamyl distearoylphosphatidyl ethanolamine:

To polyoxyethylene monomethylether (molecular weight 2000, 20 g, 10 mmol) was added benzene (75 ml) and the mixture was refluxed and dehydrated. Then, carbonyl imidazole (1,78 g, 11 mmol) was added thereto, and the mixture was refluxed for 2 hours so as to obtain an activated body. Then, distearoylphosphatidyl ethanolamine (7 g, 9.36 mmol) and triethylamine (3.1 ml, 22 mmol) were added and the mixture was refluxed for 20 hours. The reaction liquid was concentrated by an evaporator to obtained a crude product.

The crude product was purified using a C-18 reversed phase silica gel chromatography. For the C-18 reversed phase silica gel, (Bio-Gel A-1.5 m) was used and as the eluent, ethanol/water=4/1 was used. The amount of the product was 5.0 g and the yield was 10%. The result of the purity is shown in Table 3.

Comparative Example 3

(3) Synthesis of monomethyl polyoxyethylenecarbamyl 1-palmitoyl-2-oleoylphosphatidyl ethanolamine:

After dissolving polyoxyethylene monomethylether (molecular weight 2000, 5 g, 2.5 mmol) in chloroform/toluene=50/2 (wt/wt) (25 ml), triphosgene (0.89 g, 3 mmol) was added to the solution, and the reaction was carried out for 3 hours at 40° C. To the solution was added diethyl ether (75 ml) to cause precipitates. After collecting the precipitates by filtration, the precipitates were dried to obtain monomethyl polyoxyethylene chloroformate (4.7 g, 91%).

After dissolving monomethyl polyoxyethylene chloroformate (4 q, 1.94 mmol) and 1-palmitoyl-2-oleoylphosphatidyl ethanolamine (1.65 g, 2.3 mmol) in chloroform (20 ml), triethylamine (0.39 ml, 2.76 mmol) was added to the solution, and the reaction was carried out for 3 hours at 60° C.

After filtering off undissolved matters, the reaction liquid was concentrated by an evaporator. The residue formed was dissolved in water (20 ml) and by adding thereto 0.1 N hydrochloric acid (5.0 ml), the aqueous solution was acidified. To the aqueous solution was added methylene chloride (25 ml) and the product was extracted. Similarly, the extraction was repeated twice, sodium sulfate (30 g) was added to the combined extracts and the mixture was dehydrated. After filtering off sodium sulfate, the filtrate was concentrated by an evaporator. The residue formed was purified by a silica gel column chromatography to obtain 1.5 g of the objective compound. The yield was 28%. The result of the purity is shown in Table 3.

Comparative Example 4

(4) Synthesis of t-butoxycarbonylhydrazide polyoxyethylenesuccinyl phosphatidyl ethanolamine:

In chloroform (6 ml) was dissolved t-butoxycarbonylhydrazide polyoxyethylenesuccinimidyl carbonate (1 g, 0.42 mmol). Then, distearoylphosphatidyl ethanolamine (0.292 g, 0.30 mmol) and triethylamine (0.144 ml, 1.04 mmol) were added to the solution, and the reaction was carried out for 10 minutes at 45° C.

To the reaction liquid was added acetic acid (0.06 ml, 1.05 mmol) and the mixture was concentrated by an evaporator. To the residue was added water (7.5 ml) followed by dissolving, and then a small amount of chloroform was distilled off by an evaporator. The reaction liquid was placed in a Spectrapor CE dialysis tube (MWCO 300,000), and the dialysis was carried out at 4° C. with 50 mM of an isotonic sodium chloride solution (1500 ml×3) (8 to 16 hours/one dialysis). Furthermore, after carrying out dialysis with ion-exchanged water, the solution was filtered with a sterilizing filter of 0.2 μm. After liophilization, the objective product was obtained. The amount of the product was 0.55 g and the yield was 43.3%. The result of the purity is shown in Table 3.

TABLE 1

|  | Example 1 | Example 2 | Example 3 | Example 4 |
|---|---|---|---|---|
| Purity *1 | 98.4 | 99.5 | 98.4 | 98.5 |
| Yield | 52.2 | 54.6 | 65.4 | 68.6 |
| Lyso content *2 | 0.1 | 0.1 | 0.3 | 0.1 |
| Free PE content *3 | 0 | 0 | 0 | 0 |
| Free PEG derivative content *4 | 1.4 | 0.3 | 1.2 | 1.3 |
| Free triethylamine content *5 | 0 | 0 | 0 | 0 |
| Triethylamine content in free salt *6 | 0 | 0 | 0 | 0 |

TABLE 2

| Sample | Removing Ratio (%) of CDI Derivative |
|---|---|
| (1) → (2) | 27 |
| (2) → (3) | 65 |
| (3) → (4) | 40 |
| (4) → (5) | 81 |
| (5) → (6) | 85 |

TABLE 3

|  | C. Ex. 1 | C. Ex. 2 | C. Ex. 3 | C. Ex. 4 |
|---|---|---|---|---|
| Purity *1 | <84.5 | <85.6 | 84.3 | <82.6 |
| Yield | 90.8 | 18 | 28 | 43.3 |
| Lyso content *2 | 3.0 | 6.0 | 8 | 10 |
| Free PE content *3 | 1.0 | 0.2 | 0.5 | 0.3 |
| Free PEG derivative content *4 | 1.5 | 3.0 | 2 | 1.8 |
| Free triethylamine content *5 | >5 | 0.2 | 0.2 | 0.3 |
| Triethylamine content in free salt *6 | >5 | >5 | 0.0 | >5 |

C. Ex.: Comparative Example
Notes of Table 1 and Table 3:
*1 Purity: The purity of the polyalkylene oxide-modified phospholipid shown by the formula (1). (Unit: %)
*2 Lyso content: The content of monoacyl phospholipid. (Unit: %)
*3 Free PE content: The content of unreacted phospholipid. (Unit: %)
*4 Free PEG derivative content: The contents of polyethylene glycol and the derivatives thereof. (Unit: %)
*5 Free trimethylamine content: The content of triethylamine. (Unit: %)
*6 Trimethylamine content in free salt: The content of triethylamine in triethylamine phosphate. (Unit: %)

From the results of Table 1 and Table 3, it can be seen that in the production methods of the examples, the contents of impurities such as the lyso form and triethyleneamine, etc., are less as compared with the comparative examples, and the polyalkylene oxide-modified phospholipid can be produced at a high purity.

Example 5

An emulsion was prepared using monomethyl polyoxyethylenecarbamyl distearoylphosphatidyl ethanolamine of Example 3. That is, in the base made of the composition of Table 4, the oil-phase portion containing an emulsifier was uniformly dissolved by heating to 60° C., and the aqueous phase portion was added with stirring at the same temperature.

TABLE 4

| Oil-phase portion | |
|---|---|
| Cetanol | 2.0 wt. % |
| Vaseline | 2.0 wt. % |
| Squalane | 5.0 wt. % |
| Stearic acid | 0.2 wt. % |
| Fluid paraffin | 10.0 wt. % |
| Polyoxyethylene (5 mols) monooleic acid ester | 1.5 wt. % |
| Monomethyl polyoxyethylenecarbamyl distearolyl-phosphatidyl ethanolamine | 1.0 wt. % |
| Tocopherol | 0.02 wt. % |
| Perfume | Proper amount |
| Antiseptics | Proper amount |
| Aqueous phase portion: | |
| Propylene glycol | 5.0 wt. % |
| Purified water | Rest |

After storing the emulsion prepared for one month at 40° C., the emulsified state was evaluated by the following standards and the result is shown in Table 6.

3: Stable state

2: Somewhat ununiform state

1: Creaming or separated state

Also, the emulsion immediately after preparation was applied to a skin and an organoleptic test was performed. The organoleptic evaluation was performed by five special panelers. In the evaluation method, after washing the upper arm portion, the sample was applied, and the evaluations about the skin irritation directly after the application and after passing overnight were performed by the following three stages. The total points of the five panelers are shown in Table 6.

3: Usual and no abnormal symptom

2: A sense of incongruity is felt. Feel itchy a little.

1: Itchy is felt. Red coloring is observed on the skin.

Example 6

A cream was prepared using monomethyl polyoxyethylenecarbamyl distearoylphosphatidyl ethanolamine of Example 2. That is, in the base made of the composition of Table 5, the oil-phase portion containing an emulsifier was uniformly dissolved by heating to 60° C., and the aqueous phase portion was added with stirring at the same temperature.

TABLE 5

| Oil-phase portion | |
|---|---|
| Cetanol | 2.0 wt. % |
| Bees wax | 6.0 wt. % |
| Vaseline | 5.0 wt. % |
| Squalane | 34.0 wt. % |
| Glycerol monostearate | 2.0 wt. % |
| Stearic acid | 0.5 wt. % |

TABLE 5-continued

| Polyoxyethylene (8 mols) polyoxypropylene (1 mol) stearyl ether | 1.5 wt. % |
|---|---|
| Monomethyl polyoxyethylenecarbamyl distearolyl-phosphatidyl ethanolamine | 1.0 wt. % |
| Perfume | Proper amount |
| Antiseptics | Proper amount |
| Aqueous phase portion: | |
| Propylene glycol | 2.0 wt. % |
| Purified water | Rest |

About the cream prepared, the same evaluations as in Example 5 were performed. The result is shown in Table 6.

Comparative Examples 5 and 6

Using monomethyl polyoxyethylenecarbamyl distearoylphosphatidyl ethanolamine of Comparative Example 2, the same tests as Example 5 and Example 6 were carried out. The results are shown in Table 6.

TABLE 6

| | | Skin Irritativeness | | |
|---|---|---|---|---|
| | Kind of Used Compound | Directly After Coating | After Overnight | Emulsified State After Storing for 1 Month at 40° C. |
| Example 5 | Example 3 | 15 | 13 | 3 |
| Example 6 | Example 3 | 15 | 14 | 3 |
| C. Example 5 | C. Example 2 | 13 | 10 | 2 |
| C. Example 6 | C. Example 2 | 12 | 8 | 1 |

C. Example: Comparative Example

Example 7

Evaluation of stability of liposome solution:

In an egg-plant type flask were placed dipalmitoylphosphatidyl choline (1.92 g, 2.64 mmol), cholesterol (0.45 g, 1.32 mmol)., and monomethyl polyoxyethylenecarbamyl distearoylphosphatidyl ethanolamine obtained in Example 2 (0.42 g, 0.15 mmol), 50 ml of chloroform was added thereto to dissolve the components, and the solvent was removed by a rotary evaporator to form the thin film of the lipid on the inside wall of the flask. The solvent was sufficiently removed under a reduced pressure, 30 ml of a phosphoric acid-buffered isotonic sodium chloride solution having pH of 7 was added to disperse the thin film, and further, a treatment was carried out by a ultrasonic washer for 5 minutes to form a liposome solution.

The liposome solution obtained was allowed to stand for one month at room temperature. About the dispersed state of the liposome solution after one month, no change was visually observed, and the product was a homogeneous liposome solution.

Comparative Example 7

The same evaluation as Example 7 was performed using monomethyl polyoxycthylenecarbamyl distearoylphosphatidyl ethanolamine obtained in Comparative Example 2. As the result thereof, the liposome solution was not homogeneous and lipid particles were precipitated.

Example 8

Modification of asparaginase using carboxymethyl polyoxyethylenecarbamyl distearoylphosphatidyl ethanolamine:

In 50 ml of chloroform was dissolved carboxymethyl polyoxyethylenecarbamyl distearoylphosphatidyl ethanolamine (5 g, 0.86 mmol) obtained as in Example 3, N-hydroxysuccinic acid imide (0.15 g, 1.29 mmol) was added to the solution, and then dicyclohexyl carbodimide (0.27 g, 1.29 mmol) dissolved in small amount of chloroform was added, and the mixture was stirred for 2 hours at room temperature. Thereafter, undissolved matters were removed by filtration, diethyl ether was added to the solution formed, and crystals deposited were obtained by filtration. The solvent was removed under a reduced pressure and used in the following process.

In 50 ml of a phosphoric acid-buffered isotonic sodium chloride solution having pH of 7.4 was dissolved 0.1 g of asparaginase, and succinimidylcarboxymethyl polyoxyethylene calpamyldistearoylphosphatidyl ethanolamine obtained above was added, and the mixture was stirred for 4 hours at 5° C. The reaction liquid was dialyzed with a phosphoric acid-buffered isotonic sodium chloride solution having a pH of 7.4 at 4° C. to remove unreacted materials, and thereafter, the residue was lyophilized to obtain a dried product wherein asparaginase is bonded to carboxymethyl polyoxyethylenecarbamyl distearoylphosphatidyl ethanolamine.

Example 9

Preparation of a polymer micelle solution of soybean hydrogenated phosphatidylcoline using carboxymethyl polyoxyethylenecarbamyl distearoylphosphatidyl ethanolamine:

In distilled water (5 ml) were added soybean hydrogenated phosphatidylcholine (0.1 g, 0.13 mmol) and carboxymethyl polyoxyethylenecarbamyl distearoylphosphatidyl ethanolamine (1 g, 0.17 mmol) obtained as in Example 3, and the mixture was mixed with stirring. Then, distilled water (95 ml) was gradually added to the homogenous mixed solution followed by stirring to obtain a transparent and homogeneous polymer micelle solution. About the solution obtained, the particle size distribution was measured using a particle size measuring apparatus (NICOMP Model 370: manufactured by Nozaki Sangyo K. K.). As the result, the mean particle size was 35 nm.

The polymer micelle solution obtained was allowed to stand for one month at room temperature. In the state of the polymer micelle solution after one month, any change was visually observed and the solution was a homogeneous polymer micelle solution without precipitates.

This application is based on Japanese patent applications JP 2001-58160, filed Mar. 2, 2001, the entire content of which is hereby incorporated by reference, the same as if set forth at length.

What is claimed is:

1. A polyalkylene oxide-modified phospholipid represented by formula (1), which has a monoacyl phospholipid content of not more than 3% by weight and a content of a base having a nitrogen atom of not more than 0.02% by weight:

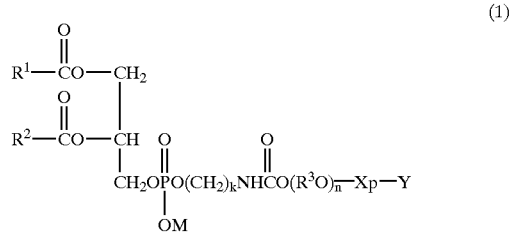

wherein $R^1CO$ and $R^2CO$ each independently represents an acyl group having from 4 to 24 carbon atoms; k represents from 1 to 6; $R^3O$ represents an oxyalkylene group having from 2 to 4 carbon atoms; n is a mean addition mol number of the oxyalkylene group having from 2 to 4 carbon atoms, and represents a number of from 10 to 800; M represents a hydrogen atom, sodium, or potassium; X represents a divalent hydrocarbon group having from 1 to 3 carbon atoms or —C(=O)(CH$_2$)$_q$—, wherein q represents from 1 to 4; p represents 0 or 1; and when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group.

2. The polyalkylene oxide-modified phospholipid according to claim 1, wherein the content of the monoacyl phospholipid is not more than 2% by weight.

3. The polyalkylene oxide-modified phospholipid according to claim 1, wherein p is 0, Y is a methyl group, and the content of the monoacyl phospholipid is not more than 0.5% by weight.

4. A method of producing a polyalkylene oxide-modified phospholipid, which comprises a process (A) of reacting an activated material of a polyalkylene oxide compound represented by formula (2) and a phospholipid represented by formula (3) in an organic solvent in the presence of an alkali metal salt whose aqueous solution shows alkalinity, the alkali metal salt being a solid salt not containing nitrogen,

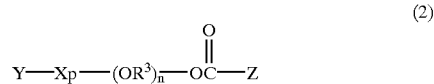

wherein $R^3O$ represents an oxyalkylene group having from 2 to 4 carbon atoms; n is a mean addition mol number of the oxyalkylene group having from 2 to 4 carbon atoms, and represents a number of from 10 to 800; X represents a divalent hydrocarbon group having from 1 to 3 carbon atoms or —C(=O)(CH$_2$)$_q$—, q represents from 1 to 4; p represents 0 or 1; when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group; and Z represents an activating group,

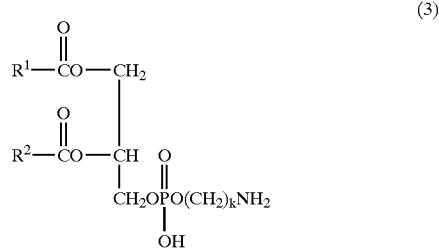

wherein $R^1CO$ and $R^2CO$ each independently represents an acyl group having from 4 to 24 carbon atoms and k represents from 1 to 6.

5. The production method according to claim 4, wherein $R^1CO$ and $R^2CO$ each is an acyl group having from 12 to 20 carbon atoms.

6. The production method according to claim 4, wherein p is 0 and Y is a methyl group.

7. The production method according to claim 4, wherein the solid salt used in the process (A) is sodium carbonate, and the organic solvent is toluene or chloroform.

8. The production method according to claim 4, which further comprises a process (B) of removing the phospholipid represented by formula (3) using ethyl acetate or acetone, after the process (A).

9. The production method according to claim 4, which further comprises a process (C) of carrying out a recrystallization using at least one of ethyl acetate and acetone as a solvent, after the process (A).

10. The production method according to claim 8, which further comprises a process (C) of carrying out a recrystallization using at least one of ethyl acetate and acetone as a solvent, after the process (A).

11. The production method according to claim 9, wherein in the process (C), at least one kind of the compound selected from the group consisting of aliphatic hydrocarbons having from 5 to 8 carbon atoms and ethers, is further used as a solvent.

12. The production method according to claim 10, wherein in the process (C), at least one kind of the compound selected from the group consisting of aliphatic hydrocarbons having from 5 to 8 carbon atoms and ethers, is further used as a solvent.

13. The production method according to claim 10, wherein the process (C) is carried out after the process (B).

14. The production method according to claim 12, wherein the process (C) is carried out after the process (B).

15. The production method according to claim 4, which further comprises a process (D) of carrying out purification using an adsorbent, after the process (A).

16. The production method according to claim 8, which further comprises a process (D) of carrying out purification using an adsorbent, after the process (A).

17. The production method according to claim 9, which further comprises a process (D) of carrying out purification using an adsorbent, after the process (A).

18. The production method according to claim 10, which further comprises a process (D) of carrying out purification using an adsorbent, after the process (A).

19. The production method according to claim 11, which further comprises a process (D) of carrying out purification using an adsorbent, after the process (A).

20. The production method according to claim 12, which further comprises a process (D) of carrying out purification using an adsorbent, after the process (A).

21. The production method according to claim 13, which further comprises a process (D) of carrying out purification using an adsorbent, after the process (A).

22. The production method according to claim 14, which further comprises a process (D) of carrying out purification using an adsorbent, after the process (A).

23. The production method according to claim 15, wherein the adsorbent used in the process (D) is an alkaline earth metal oxide, an alkaline earth metal hydroxide, an absorbent containing aluminum or silicon, or active carbon.

24. The production method according to claim 16, wherein the adsorbent used in the process (D) is an alkaline earth metal oxide, an alkaline earth metal hydroxide, an absorbent containing aluminum or silicon, or active carbon.

25. The production method according to claim 17, wherein the adsorbent used in the process (D) is an alkaline earth metal oxide, an alkaline earth metal hydroxide, an absorbent containing aluminum or silicon, or active carbon.

26. The production method according to claim 18, wherein the adsorbent used in the process (D) is an alkaline earth metal oxide, an alkaline earth metal hydroxide, an absorbent containing aluminum or silicon, or active carbon.

27. The production method according to claim 19, wherein the adsorbent used in the process (D) is an alkaline earth metal oxide, an alkaline earth metal hydroxide, an absorbent containing aluminum or silicon, or active carbon.

28. The production method according to claim 21, wherein the adsorbent used in the process (D) is an alkaline earth metal oxide, an alkaline earth metal hydroxide, an absorbent containing aluminum or silicon, or active carbon.

29. The production method according to claim 16, wherein the process (D) is carried out after the process (B).

30. The production method according to claim 18, wherein the process (D) is carried out after the process (B).

31. The production method according to claim 20, wherein the process (D) is carried out after the process (B).

32. The production method according to claim 21, wherein the process (D) is carried out after the process (B).

33. The production method according to claim 22, wherein the process (D) is carried out after the process (B).

34. The production method according to claim 4, wherein the polyalkylene oxide-modified phospholipid is a compound represented by formula (1), and has a content of a monoacyl phospholipid of not more than 3% by weight and a content of a base having a nitrogen atom of not more than 0.02% by weight,

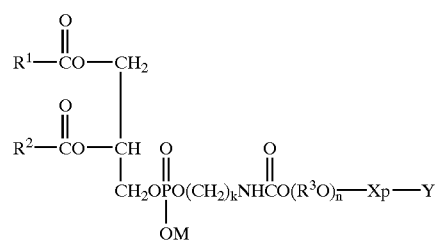

wherein $R^1CO$ and $R^2CO$ each independently represents an acyl group having from 4 to 24 carbon atoms; k represents from 1 to 6; $R^3O$ represents an oxyalkylene group having from 2 to 4 carbon atoms; n is a mean addition mol number of the oxyalkylene group having from 2 to 4 carbon atoms, and represents a number of from 10 to 800; M represents a hydrogen atom, sodium, or potassium; X represents a divalent hydrocarbon group having from 1 to 3 carbon atoms or —C(=O)(CH$_2$)$_q$—, wherein q represents from 1 to 4; p represents 0 or 1; and when p is 0, Y is a hydrogen atom or an alkyl group having from 1 to 4 carbon atoms, and when p is 1, Y is a hydrogen atom, an amino group, a carboxyl group, an aldehyde group, a glycidyl group, or a thiol group.

35. A surface active agent comprising the polyalkylene oxide-modified phospholipid according to claim 1.

36. A liposome comprising the polyalkylene oxide-modified phospholipid according to claim 1.

* * * * *